(12) United States Patent
Kocherlakota et al.

(10) Patent No.: US 12,083,104 B2
(45) Date of Patent: *Sep. 10, 2024

(54) TRIPLE COMBINATION FORMULATIONS FOR ANTIEMETIC THERAPY

(71) Applicant: LEIUTIS PHARMACEUTICALS LLP, Hyderabad (IN)

(72) Inventors: Chandrashekhar Kocherlakota, Secunderabad (IN); Nagaraju Banda, Hyderabad (IN)

(73) Assignee: LEIUTIS PHARMACEUTICALS LLP, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,011

(22) Filed: May 16, 2022

(65) Prior Publication Data

US 2022/0273630 A1    Sep. 1, 2022

Related U.S. Application Data

(63) Continuation of application No. 16/795,665, filed on Feb. 20, 2020, now Pat. No. 11,364,229, which is a continuation of application No. PCT/IB2018/056277, filed on Aug. 20, 2018.

(30) Foreign Application Priority Data

Aug. 21, 2017  (IN) .............................. 201741029536

(51) Int. Cl.
| | | |
|---|---|---|
| *A61K 31/439* | (2006.01) | |
| *A61K 31/438* | (2006.01) | |
| *A61K 31/496* | (2006.01) | |
| *A61K 31/5355* | (2006.01) | |
| *A61K 31/573* | (2006.01) | |
| *A61K 31/675* | (2006.01) | |

(52) U.S. Cl.
CPC .......... *A61K 31/439* (2013.01); *A61K 31/438* (2013.01); *A61K 31/496* (2013.01); *A61K 31/5355* (2013.01); *A61K 31/573* (2013.01); *A61K 31/675* (2013.01)

(58) Field of Classification Search
CPC .................................................. A61K 31/439
See application file for complete search history.

(56) References Cited

U.S. PATENT DOCUMENTS

| | | |
|---|---|---|
| 3,007,923 A | 11/1961 | Muller |
| 5,202,333 A | 4/1993 | Berger |
| 5,538,982 A | 7/1996 | Hagan |
| 5,691,336 A | 11/1997 | Dorn |
| 5,716,942 A | 2/1998 | Dorn |
| 6,297,375 B1 | 10/2001 | Bos |
| 7,947,724 B2 | 5/2011 | Calderari et al. |
| 7,947,725 B2 | 5/2011 | Calderari et al. |
| 8,623,826 B2 | 1/2014 | Trento |
| 9,186,357 B2 | 11/2015 | Trento |
| 9,446,052 B2 | 9/2016 | Seo et al. |
| 9,913,853 B2 | 3/2018 | Malhotra |
| 11,364,229 B2 * | 6/2022 | Kocherlakota .......... A61K 9/19 |
| 2012/0238596 A1 | 9/2012 | Kocherlakota |
| 2017/0119800 A1 | 5/2017 | Malhotra et al. |
| 2017/0216205 A1 | 8/2017 | Ottoboni |

FOREIGN PATENT DOCUMENTS

EP    2722045 B1    7/2016

OTHER PUBLICATIONS

Rudolph M. Navari, "Management of Chemotherapy-Induced Nausea and Vomiting Focus on Newer Agents and New Uses for Older Agents", 2013, Drugs, 73(3), pp. 249-262. (DOI 10.1007/s40265-013-0019-1) (Year: 2013).*
Bernardo Leon Rapoport, "Differential pharmacology and clinical utility of rolapitant in chemotherapy-induced nausea and vomiting", Feb. 2017, vol. 9, pp. 41-50. (http://dx.doi.org/10.2147/CMAR.S97543) (Year: 2017).*
International Search Report issued Oct. 31, 2018 for PCT/IB2018/056277.
Written Opinion issued Oct. 31, 2018 for PCT/IB2018/056277.
Roila et al; Guideline update for MASCC and ESMO in the prevention of chemotherapy- and radiotherapy-induced nausea and vomiting: results of the Perugia consensus conference. Annals Oncol 2010; 21 (Suppl 5): v232-243; Basch E et al. Antiemetcs: American Society of Clinical Oncology clinical practice guideline update. J Clin Oncol 2011; 29 (31): 4189-98).
F. Longo et al., Combination of Aprepitant, Palonosetron and Dexamethasone as antiemetic prophylaxis in lung cancer patients receiving multiple cycles of cisplatin-based chemotherapy, Int J Clin Pract, Aug. 2012, 66, 8, 753-757).
Sun S, Schaller J et al., Compatibility of intravenous Fosaprepitant with intravenous 5HT3 antagonists and corticosteroids. Cancer Chemother Pharmacol. Sep. 2013;72(3):509-13).
Wu G., Yeung S et al., Compatibility and Stability of Rolapitant Injectable Emulsion Admixed with Dexamethasone Sodium Phosphate. Int J Pharm Compd. Jan.-Feb. 2017;21(1):66-75).
Basch E et al. Antiemetics: American Society of Clinical Oncology clinical practice guideline update. J Clin Oncol 2011; 29(31): 4189-98).
Wu G. et al. Compatibility and Stability of VARUBI (Rolapitant) Injectable Emulsion Admixed with Intravenous Palonosetron Hydrochloride Injection and Dexamethasone Sodium Phosphate Injection; International Journal of Pharmaceutical Compounding vol. 22 No. 1 | Jan. | Feb. | 2018.
Wu G. et al. "Compatibility and Stability of Rolapitant Injectable Emulsion Admixed with Intravenous Palonosetron Hydrochloride"; International Journal of Pharmaceutical Compounding vol. 21 No. 1 | Jan. | Feb. | 2017.
Koth, Sara M.—New options and controversies in the management of chemotherapy-induced nausea and vomiting—Am J Health-Syst Pharm | vol. 74 | 2017.

(Continued)

*Primary Examiner* — Rei Tsang Shiao
(74) *Attorney, Agent, or Firm* — Sughrue Mion, PLLC

(57) ABSTRACT

The disclosure relates to chemotherapy treatments and in particular, formulations for antiemetic therapy. Parenteral formulations comprising Palonosetron, NK$_1$ receptor antagonist and a corticosteroid is provided. Also provided is a process of preparing such formulations.

20 Claims, No Drawings

(56) References Cited

OTHER PUBLICATIONS

Ryan, Julie L., "Treatment of Chemotherapy-Induced Nausea in Cancer Patients", 2010, European Oncology, 6(2), pp. 14-16. (doi: 10.17925/eoh.2010.06.02.14) (Year: 2010).
Rojas et al., "Mechanisms and latest clinical studies of new NK1 receptor antagonists for chemotherapy-induced nausea and vomiting: Rolapitant and NEPA (netupitant/palonosetron)", 2015, Cancer Treatment Reviews, 41(10), pp. 904-913. (Year: 2015).

\* cited by examiner

TRIPLE COMBINATION FORMULATIONS FOR ANTIEMETIC THERAPY

CROSS-REFERENCE TO RELATED APPLICATIONS

This application is a continuation application to U.S. application Ser. No. 16/795,665, having a filing date of Feb. 20, 2020, which is based on PCT/IB2018/056277, with an international filing date of Aug. 20, 2018, which is based upon and claims priority to Indian Patent Application No. 201741029536, having a filing date of Aug. 21, 2017, the entire contents all of which are incorporated herein by reference.

FIELD OF TECHNOLOGY

The following relates to chemotherapy treatments and in particular, formulations for antiemetic therapy.

BACKGROUND

Chemotherapy-induced nausea and vomiting (CINV) remains an important and common toxicity of cancer treatment. It presents many challenges for the continuation of treatment with the possibility of negatively affecting the outcome. Currently, antiemetic agents are used as prophylaxis against the development of CINV during the acute period (up to 24 hours after chemotherapy) and the delayed period. Newer agents like the second-generation $5\text{-}HT_3$ receptor antagonist. Palonosetron and the $NK_1$ antagonists like Aprepitant, Fosaprepitant, Netupitant, and Rolapitant offer additional clinical benefit in highly and moderately emetogenic chemotherapy.

Palonosetron belongs to the class $5\text{-}HT_3$ receptor antagonists. Palonosetron has improved antiemetic activity in the treatment of delayed chemotherapy-induced nausea and vomiting (CINV) compared to other agents in its class. Palonosetron hydrochloride Injection is marketed in the US as Aloxi® by Helsinn Healthcare. Each vial of Aloxi® contains Palonosetron hydrochloride, mannitol, and disodium edetate and citrate buffer in water for intravenous administration.

U.S. Pat. No. 5,202,333 to Jacob et al., discloses $5\text{-}HT_3$ receptor antagonists such as Palonosetron, pharmaceutical compositions containing them and methods of preparing these compounds. Further the patent also discloses the use of the compounds for the treatment of emesis, gastrointestinal disorders, central nervous system disorders, cardiovascular disorders or pain.

U.S. Pat. Nos. 7,947,724 and 7,947,725 to Giorgio et al. disclose stable liquid formulations comprising of Palonosetron at a pH from 4.0 to 6.0 and an aqueous pharmaceutically acceptable carrier including a chelating agent.

$NK_1$ receptor antagonists prevent both acute and delayed chemotherapy-induced nausea and vomiting (CINV). These agents act centrally at $NK_1$ receptors in vomiting centers within the central nervous system to block their activation by substance P released as an unwanted consequence of chemotherapy. They are effective for both moderately and highly emetogenic chemotherapy regimens. $NK_1$ receptor antagonists include drugs like Aprepitant, Fosaprepitant, Rolapitant and Netupitant.

Aprepitant is available in the form of oral suspension and capsule under the brand name Emend®. Fosaprepitant is a prodrug of Aprepitant. The meglumine salt of Fosaprepitant, Fosaprepitant dimeglumine, is available as Emend® in the form of a lyophilized powder for intravenous infusion. Netupitant is available in combination with Palonosetron in the form of oral capsules under the brand name Akynzeo®. Rolapitant is available in the form of a tablet as Varubi®.

U.S. Pat. No. 5,538,982 to Hagan et al., discloses use of $NK_1$ receptor antagonist for the treatment of emesis.

U.S. Pat. No. 5,691,336 to Dom et al, discloses the compound Fosaprepitant and further describe methods of synthesizing the compound. U.S. Pat. No. 5,716,942 also to Dom et al., discloses the use of neurokinin 1 receptor antagonist such as Fosaprepitant for the treatment of inflammatory diseases, pain or migraine, asthma, emesis and nausea.

U.S. Pat. No. 6,297,375 to Michael et al., describes methods of synthesizing and formulating Netupitant and its prodrugs.

Dexamethasone is a synthetic corticosteroid which is functionally analogous to the endogenous hormones cortisol and cortisone, but characterized by more specific pharmacokinetic and therapeutic properties and lesser side effects. Dexamethasone and other glucocorticoids or corticosteroids are said to have antiemetic effects and may improve the efficacy of antiemetic regimens in some cancer patients.

Dexamethasone acetate and Dexamethasone sodium phosphate injectables are approved in the U.S. under the brand names Decadron-LA, Decadron and Hexadrol.

Dexamethasone and its salts are described in U.S. Pat. No. 3,007,923 to Roland et al. The preparation of Dexamethasone acetate is also described.

Combinations of some of these actives are also disclosed in patents and applications. For instance, U.S. patent application 2017/216205 to Thomas et al., discloses an injectable emulsion containing a two-drug combination of Netupitant or Aprepitant and dexamethasone sodium phosphate; U.S. Pat. No. 9,446,052 to Seo et al., discloses several compositions comprising a $5\text{-}HT_3$ receptor antagonist and a corticosteroid. U.S. Pat. Nos. 9,186,357 and 8,623,826 to Fabio et al., describe an oral capsule formulation for treating CINV with a regimen of Palonosetron, $NK_1$ antagonist, particularly Netupitant in possible coadministration with Dexamethasone capsules.

The conventional art references teach various methods and formulations to treat CINV. But none of the references disclose a single parenteral formulation comprising all the three actives i.e Palonosetron, $NK_1$ antagonist and a corticosteroid. Accordingly, there exists a need to develop improved formulations for treating CINV with minimal discomfort to the patients. The present invention addresses this need.

SUMMARY

An aspect relates to a parenteral formulation comprising Palonosetron, $NK_1$ receptor antagonist and a corticosteroid.

One aspect of embodiments of the invention provides parenteral formulation comprising of Palonosetron, $NK_1$ receptor antagonist selected from Fosaprepitant, Aprepitant, Netupitant and Rolapitant; and a corticosteroid.

Another aspect of embodiments of the invention provides parenteral formulation comprising Palonosetron, $NK_1$ receptor antagonist selected from Fosaprepitant, Aprepitant, Netupitant and Rolapitant; and a corticosteroid selected from Dexamethasone and Methylprednisolone.

Yet another aspect of embodiments of the invention provides parenteral formulation comprising Palonosetron, $NK_1$ receptor antagonist selected from Fosaprepitant, Aprepitant, Netupitant and Rolapitant; and a corticosteroid selected from Dexamethasone and Methylprednisolone, wherein the total impurities are less than 10%.

DETAILED DESCRIPTION

In the context of embodiments of the invention, pharmaceutically acceptable salts, solvates, polymorphs, hydrates and anhydrous forms of any of the drugs i.e Palonosetron, $NK_1$ receptor antagonist and corticosteroid may be used. The $NK_1$ receptor antagonists of embodiments of the invention can be Fosaprepitant, Aprepitant, Rolapitant or Netupitant. The corticosteroid may be selected from Methylprednisolone and Dexamethasone.

In the context of embodiments of the present invention, "parenteral formulation" is intended to cover (i) a ready to use formulation, (ii) a ready to dilute formulation, (iii) a lyophilized formulation. (iv) a kit, (v) a suspension and (vi) an emulsion.

As used herein "ready to use" formulation refers to liquid formulations that are intended to be used as such without further dilution.

As used herein "ready to dilute" formulation refers to liquid formulations that are intended to be used after dilution.

As used herein "lyophilized formulation" refers to formulations that are intended to be used upon reconstitution with a diluent with or without further dilution.

As used herein "kit" formulation comprises one or more actives provided as lyophilized powders and the remaining are provided in the form of a solution for admixing with the lyophilized active(s).

The term "about" is meant to encompass a pH range of 0.5 from the specified value or range.

CINV strongly affects the quality of life of cancer patients. Nausea and vomiting still rank among the most distressing side effects. Certain chemotherapy regimens have a high risk of CINV (>90% frequency of emesis).

For this reason, the antiemetic guidelines suggest using a triple combination of $NK_1$ receptor antagonists, 5 $HT_3$ receptor antagonists and Dexamethasone. (Roila et al: *Guideline update for MASCC and ESMO in the prevention of chemotherapy-and radiotherapy-induced nausea and vomiting: results of the Perugia consensus conference. Annals Oncol* 2010; 21 (Suppl 5): v232-243: Basch E et al. *Antiemetics: American Society of Clinical Oncology clinical practice guideline update. J Clin Oncol* 2011: 29(31): 4189-98).

Longo et al studied the efficacy of triple combination of Aprepitant, Palonosetron and Dexamethasone in cancer patients receiving highly emetogenic chemotherapy and reported high control of CINV during the first chemotherapy cycle and found that the antiemetic protection was maintained over multiple cycles of chemotherapy. (F. Longo et al., *Combination of Aprepitant, Palonosetron and Dexamethasone as antiemetic prophylaxis in lung cancer patients receiving multiple cycles of cisplatin-based chemotherapy. Int J Clin Pract.* August 2012, 66, 8, 753-757) The administration was carried out using the individually available formulations which requires multiple injections thereby causing further discomfort to the patient.

Hence there is an unmet need for administering the antiemetic agents in a single formulation which would aid in minimizing the discomfort to the patients. However, formulations that have more than one active are difficult to stabilize when compared to single active formulations. This may be because of many reasons including the incompatibility of the active with the excipients and/or interaction between the two actives.

Sun et al studied the compatibility of intravenous Fosaprepitant with intravenous 5HT3 antagonists and corticosteroids and found that the combination of Palonosetron, Fosaprepitant and corticosteroid (Dexamethasone sodium phosphate or Methylprednisolone sodium succinate) is incompatible (Sun S, Schaller J et al., *Compatibility of intravenous Fosaprepitant with intravenous* 5HT3 *antagonists and corticosteroids. Cancer Chemother Pharmacol.* 2013 September; 72(3):509-13).

Studies on admixtures of Rolapitant and Dexamethasone showed stability being maintained for at least 6 hours when stored at 20° C. to 25° C. irrespective of the container. (Wu Gl, Yeung S et al., *Compatibility and Stability of Rolapitant Injectable Emulsion Admixed with Dexamethasone Sodium Phosphate. Int J Pharm Compd.* 2017 January-February: 21(1):66-75). Similar studies with Rolapitant in combination with Palonosetron showed that the solution is stable only for 48 hours at room temperature.

All the above studies teach that a combination of Palonosetron, $NK_1$ receptor antagonist with a corticosteroid show stability only for few hours.

The inventors of embodiments of the present invention have developed a novel stable parenteral formulation that comprises Palonosetron. $NK_1$ receptor antagonist selected from Fosaprepitant, Aprepitant, Netupitant and Rolapitant and a corticosteroid to address the unmet need in the conventional art.

An embodiment of the invention relates to parenteral formulation comprising:
i. Palonosetron
ii. $NK_1$ receptor antagonist
iii. Corticosteroid, and
iv. Pharmaceutically acceptable excipients Another embodiment of the invention relates to parenteral formulation comprising:
i. Palonosetron Hydrochloride
ii. $NK_1$ receptor antagonist selected from the group comprising Fosaprepitant, Aprepitant, Rolapitant and Netupitant
iii. Corticosteroid selected from Dexamethasone and Methylprednisolone and
iv. Pharmaceutically acceptable excipients Yet another embodiment of the invention provides parenteral formulation comprising:
i. Palonosetron Hydrochloride
ii. $NK_1$ receptor antagonists selected from the group comprising Fosaprepitant, Aprepitant, Rolapitant and Netupitant
iii. Corticosteroid selected from Dexamethasone and Methylprednisolone and
iv. Pharmaceutically acceptable excipients selected from the group comprising stabilizing agents, solubilizing agents, buffering agents, pH adjusting agents and solvents.

An embodiment of the invention provides parenteral formulation having a pH in the range of about 4-12. More specifically, the embodiments provide parenteral formulation having a pH in the range of 6-10.

Suitable stabilizing agents and solubilizing agents are selected from surfactants, chelating agents and cyclodextrins. Suitable cyclodextrins include the following, but not limited to α, β, and γ-cyclodextrin and cyclodextrins modified with alkyl-, hydroxyalkyl-, dialkyl-, and sulfoalkyl-ether modified cyclodextrins such as methyl or hydroxypropyl β-cyclodextrins (HPβCD), methyl-and-ethyl-β-cyclodextrin, sulfoalkylether-substituted beta-cyclodextrin, sulfobutylether-β-cyclodextrin (SBECD) and the like. Suitable surfactants include amphoteric, non-ionic, cationic or anionic surfactants such as sodium laurel sulfate, polyoxyethylene alkyl aryl ethers, polyethylene glycol fatty acid esters, polyoxyethylene-polyoxypropylene block co-polymers, polyoxyethylene sorbitan fatty acid ester such as polysorbate, sorbitan fatty acid mono esters, polyoxyethylene castor oil derivatives such as polyoxyl castor oil, polyoxyl hydrogenated castor oil, monooleate, monolaurate, monopalmitate, monostearate, dioctyl sulfosuccinate, lecithin, polyoxyethylene fatty acid glycerides, poloxamer, cremophor, cetrimide, polyethylene glycols and the like. Chelating agents can be selected from, but not limited to DOTA (1,4,7,10-tetraazacyclododecane-1,4,7,10-tetraacetic acid), DTPA (diethylene triamine-N,N,N',N'',N''-penta acetate), EDTA (Ethylenediaminetetraacetic acid) or its salts. Meglumine can also be used as a solubilizing agent.

Suitable buffering agents include the following, but not limited to buffers such as aconitic, citrate buffer, sodium carbonate, sodium bicarbonate, tartarate, benzoate, lactate, acetate buffer, phosphate buffer, metabolic acids, glutaric, malic, succinic, aspartic acid and carbonic acid, alkali or alkaline earth salt of one of these acids, Tris buffer and amino acid buffers such as arginine, histidine, glycine, lysine and glutamic acid.

pH adjusting agents may be selected from acids such as acetic, boric, citric, lactic, phosphoric and hydrochloric acids; bases such as sodium hydroxide, sodium phosphate, sodium borate, sodium citrate, sodium acetate and sodium lactate.

Suitable solvents can be selected from glycerine, ethanol, propylene glycol, PEG, dimethylacetamide, N-methylpyrrolidone, transcutol, glycofurol, water and mixtures thereof.

The parenteral formulation of embodiments of the present invention may contain anti-oxidants and preservatives such as butylated hydroxyanisole (BHA), butylated hydroxyl toluene (BHT), citric acid, tocopherol, sorbic acid, monothioglycerol, ascorbic acid, boric acid, propyl gallate, aminoacids and mixtures thereof; tonicity modifiers such as dextrose, mannitol, potassium chloride, sodium chloride; bulking agents such as mannitol, lactose, trehalose, inositol, glucose, sucrose, maltose, xylitol, starches, sorbitol, dextrose and sodium chloride; oils such as soybean oil, sesame oil, cotton seed oil, safflower oil, sunflower oil, arachis oil, corn oil, castor oil and olive oil.

Evaluation of Buffer System

The inventors of this formulation have surprisingly developed a stable parenteral formulation containing all the three actives, wherein the formulation has less than 10% impurities.

This is particularly challenging because Fosaprepitant rapidly gets converted to Aprepitant in aqueous solution which often precipitates out due to low aqueous solubility. The inventors carried out experiments with various buffering agents to determine suitable buffer system for Fosaprepitant. The formulations were stressed at 60° C. for 12 hours. The samples obtained were filtered and analysis was carried out to determine the solubility of Aprepitant in the buffer system.

Fosaprepitant (1.5 mg/ml) and kleptose (73.6 mg/ml) were dissolved in the buffer systems tabulated below to evaluate their suitability.

TABLE 1

Evaluation of buffer system

| Buffer System | After 12 hours at 60° C. | |
|---|---|---|
| | pH | % Aprepitant |
| Arginine + Tartaric acid | 7.60 | 2.73 |
| Arginine + Isoleucine | 7.93 | 3.23 |
| Arginine + Glycine | 8.57 | 4.66 |
| Arginine + Succinic Acid | 9.06 | 4.50 |
| Arginine + Aspartic acid | 8.82 | 5.53 |
| Tris + Tartaric acid | 8.25 | 4.02 |
| Tris + Isoleucine | 8.22 | 3.51 |
| Tris + Glycine | 8.26 | 3.64 |
| Tris + Aspartic acid | 8.50 | 3.12 |
| Tris + Succinic acid | 8.35 | 4.23 |

From the above data it is observed that Aprepitant has best solubility in Aspartic Acid+Arginine buffer system.

To further improve the solubility of Fosaprepitant and Aprepitant in the formulation, inventors carried out stress studies using suitable solubilizer in the formulation. The formulations were prepared in the Arginine+Aspartic acid buffer system comprising different concentrations of meglumine. The samples were stressed at 60° C. for 24 hours and were analyzed after filtration.

TABLE 2

Effect of Meglumine on solubility

| Concentration of meglumine (mg/ml) | % Aprepitant |
|---|---|
| Nil | 1.2 |
| 0.48 | 2.2 |
| 0.95 | 5.7 |
| 1.43 | 4.6 |
| 1.90 | 4.2 |

It was observed that meglumine improves the solubility of Aprepitant in the buffer system.

Concentration Ranges of Actives

In some aspects of embodiments of the invention the fill volume of liquid formulations prepared according to embodiments of the invention ranges from about 1 mL to 500 mL, more preferably 5 mL to 200 mL. The concentration of $NK_1$ receptor antagonist, Palonosetron and corticosteroid varies accordingly. The concentration of Fosaprepitant ranges from about 0.5 mg/ml to 10 mg/ml, the concentration of Aprepitant ranges from about 0.5 mg/ml to 100 mg/ml, the concentration of Rolapitant ranges from about 0.5 mg/ml to 20 mg/ml, the concentration of Netupitant ranges from about 0.5 mg/ml to 100 mg/ml. The concentration of Palonosetron ranges from about 0.0005 mg/ml to 5 mg/ml. The concentration of dexamethasone ranges from about 0.01 mg/ml to 50 mg/ml. The concentration of Methylprednisolone ranges from about 1 mg/ml to 100 mg/ml.

Effect of Primary Packing on Stability

The formulations prepared according to embodiments of the invention comprising all the three actives are filled in suitable containers selected from glass or polymer containers. The containers include vials, ampoules, syringes, bags and bottles with sizes ranging from 1 ml to 500 ml. Polymer material include cyclic olefin copolymer (COC), cyclic olefin polymer (COP), an olefin polymer, a polypropylene polymer, a polyvinyl chloride polymer (PVC), polyethylene, modified propylene, copolyester, polycarbonate polymer and the like. Studies were carried out to check the stability of the formulation in various containers. The packing materials used were; type-I clear glass vial, COC vials, COP vials, and infusion bag.

TABLE 3

Stability of the formulation in different primary packs

| Pack details | Initial | COC vials | COP vials | PVC Infusion bag | USP Type-I glass vial |
|---|---|---|---|---|---|
| Stability Condition | Initial | | | 1 Week, 40° C. | |
| Description | CCS | CCS | CCS | CCS | CCS |
| pH | 8.54 | 8.52 | 8.57 | 8.52 | 8.53 |
| Palonosetron | | | | | |
| % Assay | 104.9 | 104.8 | 104.7 | 104.2 | 104.4 |
| Total Impurities | 0.29 | 0.56 | 0.53 | 0.58 | 0.56 |
| Dexamethasone | | | | | |
| % Assay | 98.6 | 99.9 | 98.8 | 99.9 | 98.7 |
| Total Impurities | 1.32 | 1.38 | 1.29 | 1.24 | 1.26 |
| Fosaprepitant | | | | | |
| % Assay | 98.3 | 97.2 | 95.9 | 96.4 | 95.8 |
| Aprepitant | 0.5 | 2.63 | 2.60 | 2.64 | 2.60 |
| Total Impurities | 0.71 | 2.88 | 2.85 | 2.90 | 2.79 |

*CCS: Clear, colorless solution.

Suability Studies

The formulations prepared according to embodiments of the invention were studied for stability at 2-8° C. and 25° C.

TABLE 4

Stability data of the products prepared according to examples 2 and 3
Stability data of the products prepared according to examples 2 and 3

| | Example 2 | | | Example 3 | | |
|---|---|---|---|---|---|---|
| Condition | Initial | 3 M, 2-8° C. | 3 M_25° C. | Initial | 3 M, 2-8° C. | 3 M, 25° C. |
| Palonosetron | | | | | | |
| Assay | 103.7 | 105.5 | 105.4 | 105.5 | 106 | 105.3 |
| Total Impurities | 0.21 | 0.36 | 0.67 | 0.23 | 0.37 | 0.70 |
| Dexamethasone | | | | | | |
| Assay | 102.1 | 103.2 | 102.9 | 100.1 | 100.8 | 101.1 |
| Total Impurities | 1.19 | 1.24 | 1.16 | 1.08 | 1.00 | 0.99 |
| Fosaprepitant | | | | | | |
| Assay | 100.6 | 98.6 | 96.4 | 103.3 | 100.5 | 94.7 |
| Aprepitant | 0.41 | 0.75 | 2.98 | 0.42 | 0.58 | 4.32 |
| Total Impurities | 0.92 | 1.26 | 3.41 | 0.94 | 1.05 | 4.68 |

The above data shows excellent stability of the formulation.

Types of Formulations

The formulations of embodiments of the present invention can be administered as a ready to use solution, ready to dilute solution; lyophilized formulation; suspension, emulsion and the like. The formulations can be made by standard manufacturing techniques known in the art.

The following examples further describe certain specific aspects and embodiments of embodiments of the present invention and also outline the quantitative proportions of the actives and excipients in the combination formulation. It is to be understood that the examples are given by way of illustration only and are not intended to limit the scope of embodiments of the invention in any manner.

Example 1

Ready to Use Formulation

| S. No | Ingredients | Quantity/mL (mg) |
|---|---|---|
| 1. | Fosaprepitant dimeglumine | 1.0 |
| 2. | Palonosetron hydrochloride | 0.00167 |
| 3. | Dexamethasone sodium phosphate | 0.08 |
| 4. | Hydroxy propyl beta cyclodextrin(Kleptose) | 49.06 |
| 5. | Ethylenediamine tetraacetic acid | 0.2507 |
| 6. | Sodium carbonate | 0.16 |
| 7. | Sodium bicarbonate | 1.3333 |
| 8. | Sodium chloride | 7.0 |
| 9. | Sodium hydroxide | Qs to adjust pH 8.0-8.5 |
| 10. | Hydrochloric acid | Qs to adjust pH 8.0-8.5 |
| 11. | Water for injection | Qs to 1 mL |

Manufacturing Process:

Water for injection was taken in a compounding vessel and kleptose was added and stirred. The above solution was cooled to 2-8° C. Fosaprepitant dimeglumine was added to the above solution. Ethylenediamine tetraacetic acid was added followed by the addition of sodium carbonate and sodium bicarbonate. Palonosetron hydrochloride was added followed by the addition of Dexamethasone sodium and stirred. Sodium chloride was added to the above solution and pH of the solution was adjusted with sodium hydroxide and hydrochloric acid. The solution was filtered, followed by stoppering and sealing of the vials.

Example 2

Ready to Use Formulation

| S. No | Ingredients | Quantity/mL (mg) |
|---|---|---|
| 1. | Fosaprepitant dimeglumine | 2.0 |
| 2. | Palonosetron hydrochloride | 0.00333 |
| 3. | Dexamethasone sodium phosphate | 0.16 |
| 4. | Kleptose (Hydroxy propyl Betadex) | 98.12 |
| 5. | Ethylenediamine tetraacetic acid | 0.5013 |
| 6. | Sodium carbonate | 0.32 |
| 7. | Sodium bicarbonate | 2.6667 |
| 8. | Sodium chloride | 5.0 |
| 9. | Sodium hydroxide | Qs to adjust pH 8.0-8.5 |
| 10. | Hydrochloric acid | Qs to adjust pH 8.0-8.5 |
| 11. | Water for injection | Qs to 1 mL |

Manufacturing Process:

Water for injection was taken in a compounding vessel and kleptose was added and stirred. The above solution was cooled to 2-8° C. Fosaprepitant dimeglumine was added to the above solution. Ethylenediamine tetraacetic acid was added followed by the addition of sodium carbonate and sodium bicarbonate. Palonosetron hydrochloride was added followed by the addition of Dexamethasone sodium and stirred. Sodium chloride was added to the above solution and pH of the solution was adjusted with sodium hydroxide and hydrochloric acid. The solution was filtered, followed by stoppering and sealing of the vials.

Example 3

Ready to Use Formulation

| S. No | Ingredients | Quantity/mL (mg) |
|---|---|---|
| 1. | Fosaprepitant dimeglumine | 1.5 |
| 2. | Palonosetron hydrochloride | 0.0025 |
| 3. | Dexamethasone sodium phosphate | 0.12 |
| 4. | Hydroxy propyl Beta cyclodextrin (Kleptose) | 73.59 |
| 5. | Ethylenediamine tetraacetic acid | 0.3760 |
| 6. | Sodium carbonate | 0.24 |
| 7. | Sodium bicarbonate | 2.0 |
| 8. | Sodium chloride | 6.0 |
| 9. | Sodium hydroxide | Qs to adjust pH 8.0-8.5 |
| 10. | Hydrochloric acid | Qs to adjust pH 8.0-8.5 |
| 11. | Water for injection | Qs to 1 mL |

Manufacturing Process:

Water for injection was taken in a compounding vessel and kleptose was added and stirred. The above solution was cooled to 2-8° C. Fosaprepitant dimeglumine was added to the above solution. Ethylenediamine tetraacetic acid was added followed by the addition of sodium carbonate and sodium bicarbonate. Palonosetron hydrochloride was added followed by the addition of Dexamethasone sodium and stirred. Sodium chloride was added to the above solution and pH of the solution was adjusted with sodium hydroxide and hydrochloric acid. The solution was filtered, followed by stoppering and sealing of the vials.

Example 4

Read to Dilute Formulation

| S. No | Ingredients | Quantity/mL (mg) |
|---|---|---|
| 1. | Fosaprepitant dimeglumine | 3.0 |
| 2. | Palonosetron hydrochloride | 0.005 |
| 3. | Dexamethasone sodium phosphate | 0.24 |
| 4. | Kleptose (Hydroxy propyl Betadex) | 147.18 |
| 5. | Ethylenediamine tetraacetic acid | 0.752 |
| 6. | Sodium carbonate | 0.48 |
| 7. | Sodium bicarbonate | 4.0 |
| 8. | Sodium chloride | 2.0 |
| 9. | Sodium hydroxide | Q.s to adjust pH |
| 10. | Hydrochloric acid | Q.s to adjust pH |
| 11. | Water for injection | Q.s to 1 mL |

Manufacturing Process:

Water for injection was taken in a compounding vessel and kleptose was added and stirred. The above solution was cooled to 2-8° C. Fosaprepitant dimeglumine was added to the above solution. Ethylenediamine tetraacetic acid was added followed by the addition of sodium carbonate and sodium bicarbonate. Palonosetron hydrochloride was added followed by the addition of Dexamethasone sodium and stirred. Sodium chloride was added to the above solution and pH of the solution was adjusted with sodium hydroxide and hydrochloric acid. The solution was filtered, followed by stoppering and sealing of the vials.

Example 5

Emulsion Formulation

| S. No | Ingredients | Quantity/mL (mg) |
|---|---|---|
| 1. | Aprepitant | 15 mg |
| 2. | Dexamethasone Sodium Phosphate | 1.20 mg |
| 3. | Palonosetron | 0.025 mg |
| 4. | Castor Oil | 50.00 mg |
| 5. | Polysorbate-80 | 40.00 mg |
| 6. | Glycerine | 22.00 mg |
| 7. | Sorbic acid | 1.00 mg |
| 8. | Sodium acetate | 0.50 mg |
| 9. | Boric acid | 1.00 mg |
| 10. | Sodium EDTA | 0.20 mg |
| 11. | Sodium Hydroxide/Hydrochloric acid | Q.s |
| 12. | Water for Injection | Q.s to 1 ml |

Manufacturing Process

Aprepitant was dissolved in preheated castor oil at temperature maintained between 50° C. to 75° C. The aqueous phase was prepared by dissolving polysorbate-80, glycerin, sodium acetate, boric acid, sorbic acid, and disodium EDTA in water for injection at about 70° C. The oil phase and aqueous phase were mixed by using high shear mixer (Polytron) at about 7500 rpm at a temperature of about 70° C. for approximately 60 minutes to form a coarse emulsion. The emulsion was cooled to room temperature and passed through high pressure homogenizer at 70±5° C. (Pressure: 17000 psi & No. of Passes: 05) to get a fine emulsion. Palonosetron hydrochloride and Dexamethasone sodium phosphate were dissolved in the remaining water for injection. The solution was added to the emulsion of Aprepitant and stirred to achieve uniformity. pH was adjusted to desired target between 3.0 and 11.0 using 0.1N sodium hydroxide or hydrochloric acid.

The emulsion was further processed aseptically by filtration and filled into suitable primary packaging containers. The emulsion was analyzed and the results are shown in table 5:

TABLE 5

| PH | 5.06 |
|---|---|
| Osmolality | 521 |
| Globule Size Distribution | |
| d10 (nm) | 133 |
| d50 (nm) | 230 |
| d90 (nm) | 360 |
| Z-Average | 230 |

Example 6

Manufacturing Process

| S. No | INGREDIENTS | QUANTITY (MG/ML) |
|---|---|---|
| 1 | APREPITANT | 100 |
| 2 | DEXAMETHASONE SODIUM PHOSPHATE | 8 |
| 3 | PALONOSETRON | 0.16 |
| 4 | POLYSORBATE-20 | 8 |
| 5 | CITRIC ACID MONOHYDRATE | 3.33 |
| 6 | DISODIUM HYDROGEN PHOSPHATE ANHYDROUS | 3.33 |

-continued

| S. No | INGREDIENTS | QUANTITY (MG/ML) |
|---|---|---|
| 7 | SODIUM DIHYDROGEN PHOSPHATE MONOHYDRATE | 1.6 |
| 8 | PEG 4000 | 20 |
| 9 | SODIUM HYDROXIDE OR HYDROCHLORIC ACID | 1.89 |
| 10 | WATER FOR INJECTION | Q.S TO 1 ML |

The aqueous phase was prepared by dissolving polysorbate-20 in water for injection at room temperature. Aprepitant was dispersed into the solution under homogenization at about 1000 rpm for 30 minutes approximately so that a suspension containing about 25% w/w solid content is obtained. The suspension was then milled in a bead mill with 55% occupancy, using 0.8 mm beads, at an rpm of 1000 and for a duration of about 2 hrs. Palonosetron hydrochloride and Dexamethasone sodium phosphate were dissolved separately in water for injection and added to the suspension under stirring. PEG4000, citric acid monohydrate, disodium hydrogen phosphate, sodium dihydrogen phosphate, and sodium hydroxide were dissolved into the suspension under stirring. The pH was adjusted to desired target between 3.0 and 11.0 using 0.1N sodium hydroxide or hydrochloric acid solution and final weight was made up using water for injection. The suspension was analyzed and the results are shown below:

| Description | White to off white suspension |
|---|---|
| pH | 6.01 |
| Particle Size Distribution | |
| d10 (nm) | 0.3 |
| d50 (nm) | 1.1 |

Example 7

Lyophilized Formulation

| S. No | Ingredients | Quantity (mg)/Vial |
|---|---|---|
| 1. | Fosaprepitant dimeglumine | 150 |
| 2 | Dexamethasone phosphate | 12 |
| 3 | Palonosetron hydrochloride | 0.25 |
| 4 | Hydroxypropyl beta cyclodextrin (HPBCD) | 1000 |
| 5 | Disodium edetate | 37.6 |
| 6 | Sodium hydroxide | Qs to adjust pH 7.0 |
| 7 | Hydrochloric acid | Qs to adjust pH 7.0 |
| 8 | Water for injection | QS |

Manufacturing Process

Water for injection was taken in a compounding vessel and HPBCD was added and stirred. The above solution was cooled to 2-8° C. Fosaprepitant dimeglumine was added to the above solution. Disodium edetate was added followed by the addition of Palonosetron hydrochloride. Dexamethasone phosphate was added and stirred. pH of the solution was adjusted with sodium hydroxide and hydrochloric acid. The solution was filled in vials and lyophilized.

Example 8

Kit with Fosaprepitant Lyophilizate

| S. No | Ingredient | Quantity (mg)/Vial |
|---|---|---|
| | Fosaprepitant lyophilizate | |
| 1. | Fosaprepitant | 150 |
| 2. | Hydroxypropyl beta cyclodextrin (HPBCD) | 1000 |
| 3. | Disodium edetate | 18.8 |
| 4. | Sodium Hydroxide | Qs to adjust pH 7.0 |
| 5. | Hydrochloric acid | Qs to adjust pH 7.0 |

| | | Quantity (mg)/10 mL |
|---|---|---|
| Liquid injection formulation with Palonosetron and Dexamethasone | | |
| 1. | Dexamethasone Phosphate | 12 |
| 2. | Palonosetron hydrochloride | 0.25 |
| 3. | Dibasic sodium phosphate dihydrate | 1323 |
| 4. | Monobasic sodium phosphate monohydrate | 94 |
| 5. | Disodium edetate | 18.8 |
| 6. | Sodium Hydroxide | Qs to adjust pH 7.0 |
| 7. | Hydrochloric acid | Qs to adjust pH 7.0 |
| 8. | Water | QS to 10 mL |

Manufacturing Process

Water for injection was taken in a compounding vessel and HPBCD was added and stirred. The above solution was cooled to 2-8° C. Fosaprepitant dimeglumine was added to the above solution. Disodium edetate was added. pH of the solution was adjusted with sodium hydroxide and hydrochloric acid. The solution was filled in vials and lyophilized.

Water for injection was taken in a compounding vessel and dibasic sodium phosphate dihydrate and monobasic sodium phosphate monohydrate were added Palonosetron hydrochloride was added followed by the addition of Dexamethasone phosphate and stirred. Disodium edetate was added. pH of the solution was adjusted with sodium hydroxide and hydrochloric acid. The solution was filtered, followed by stoppering and sealing of the vials.

Fosaprepitant lyophilizate and liquid injection formulation with Palonosetron and Dexamethasone are supplied together as a kit.

Example 9

Ready to Dilute Formulation

| S. No | Ingredient | Quantity (mg)/20 mL |
|---|---|---|
| | Fosaprepitant | 150 |
| | Dexamethasone phosphate | 12 |
| | Palonosetron hydrochloride | 0.25 |
| | Polysorbate 80 | 100 |
| | Disodium edetate | 37.6 |
| | Sodium Hydroxide | Qs to adjust pH 9.0 |
| | Hydrochloric acid | Qs to adjust pH 9.0 |
| | Water for injection | QS to 20 mL |

Manufacturing Process

Water for injection was taken in a compounding vessel and cooled to 2-8° C. Fosaprepitant dimeglumine was added to the above solution. Disodium edetate was added followed by the addition of Palonosetron hydrochloride and Dexamethasone phosphate and stirred. Polysorbate 80 was added. pH of the solution was adjusted with sodium hydroxide and hydrochloric acid. The solution was filtered, followed by stoppering and sealing of the vials.

Example 10

Kit with Fosaprepitant Lyophilizate

| S. No | Ingredients | Quantity (mg)/Vial |
|---|---|---|
| | Fosaprepitant lyophilizate | |
| | Fosaprepitant | 150 |
| | Polysorbate 80 | 100 |
| | Disodium edetate | 18.8 |
| | Sodium hydroxide | Qs to adjust pH 5.0 |
| | Hydrochloric acid | Qs to adjust pH 5.0 |

| | | Qty. (mg)/10 mL |
|---|---|---|
| Liquid injection formulation with Palonosetron and Dexamethasone | | |
| | Dexamethasone phosphate | 12 |
| | Palonosetron | 0.25 |
| | Sodium carbonate anhydrous | 24 |
| | Sodium bicarbonate | 200 |
| | Disodium edetate | 18.8 |
| | Sodium hydroxide | Qs to adjust pH 9.0 |
| | Hydrochloric acid | Qs to adjust pH 9.0 |
| | Water | QS to 10 mL |

Manufacturing Process

Water for injection was taken in a compounding vessel and cooled to 2-8° C. Fosaprepitant dimeglumine was added to the above solution. Disodium edetate was added followed by the addition of polysorbate 80. pH of the solution was adjusted with sodium hydroxide and hydrochloric acid. The solution was filled in vials and lyophilized.

Water for injection was taken in a compounding vessel and sodium carbonate anhydrous and sodium bicarbonate were added. Palonosetron hydrochloride was added followed by the addition of Dexamethasone phosphate and stirred. Disodium edetate was added. pH of the solution was adjusted with sodium hydroxide and hydrochloric acid. The solution was filtered, followed by stoppering and sealing of the vials.

Fosaprepitant lyophilizate and liquid injection formulation with Palonosetron and Dexamethasone are supplied together as a kit.

Example 11

Ready to Dilute Formulation with Rolapitant

| S. No | Ingredients | Quantity (mg/mL) |
|---|---|---|
| | Rolapitant | 9 |
| | Dexamethasone phosphate | 1 |
| | Palonosetron hydrochloride | 0.0125 |
| | Hydroxypropyl beta cyclodextrin | 367.95 |
| | Dibasic sodium phosphate dihydrate | 13.23 |
| | Monobasic sodium phosphate monohydrate | 0.94 |
| | Disodium edetate | 1.88 |
| | Sodium hydroxide | Qs to adjust pH 7.0 |
| | Hydrochloric acid | Qs to adjust pH 7.0 |
| | Water | QS to 1 mL |

Manufacturing Process

Water for injection was taken in a compounding vessel and hydroxypropyl beta cyclodextrin was added and stirred. Rolapitant was added to the above solution. Disodium edetate was added followed by the addition of dibasic sodium phosphate dihydrate and monobasic sodium phosphate monohydrate. Palonosetron hydrochloride was added followed by Dexamethasone phosphate and stirred. pH of the solution was adjusted with sodium hydroxide and hydrochloric acid. The solution was filtered, followed by stoppering and sealing of the vials.

Example 12

Ready to Use Formulation

| S. No | Ingredients | mg/mL |
|---|---|---|
| 1. | Fosaprepitant Dimeglumine | 3 |
| 2. | Palonosetron Hydrochloride | 0.005 |
| 3. | Dexamethasone Sodium phosphate | 0.24 |
| 4. | Kleptose | 100 |
| 5. | Meglumine | 1.904 |
| 6. | L-Aspartic acid | 2 |
| 7. | L-Arginine | 2 |
| 8. | Disodium EDTA | 0.05 |
| 9. | Ultra-pure Water | QS to 1 mL |

QS: Quantity sufficient

Manufacturing Process:

Required quantity of L-Aspartic acid and L-Arginine were added to water followed by kleptose and stirred. Required quantity of meglumine and disodium EDTA were added. The solution was cooled to 2-8° C. Fosaprepitant dimeglumine was added followed by Palonosetron hydrochloride and Dexamethasone sodium phosphate and stirred till a clear solution was obtained.

TABLE 6

Stability data of the product prepared according to example 12.

| Stability Condition | Initial | 1 Month 2-8° C. | 2 Months 2-8° C. | 3 Months 2-8° C. | 6 Months 2-8° C. |
|---|---|---|---|---|---|
| pH | 8.60 | 8.76 | 8.91 | 8.90 | 8.88 |
| Description | Clear solution | Clear solution | Clear solution | Clear solution | Clear solution |
| Palonosetron | | | | | |
| % Assay | 101.6 | 102.0 | 101.2 | 101.1 | 101.4 |
| % Total Impurities | 0.08 | 0.20 | 0.15 | 0.20 | 0.22 |
| Dexamethasone | | | | | |
| % Assay | 99.5 | 99.6 | 99.4 | 97.6 | 98 |
| Total Impurities | 0.76 | 1.62 | 1.54 | 1.49 | 1.51 |
| Fosaprepitant | | | | | |
| % Assay | 98.6 | 98.9 | 99.8 | 98.0 | 98.1 |
| % Aprepitant | 0.76 | 0.80 | 0.89 | 0.94 | 0.98 |
| % Total Impurities | 1.19 | 1.24 | 1.29 | 1.33 | 1.38 |

Example 13

Ready to Use Formulation

| S. No | Ingredients | mg/mL |
|---|---|---|
| 1. | Fosaprepitant Dimeglumine | 3 |
| 2. | Palonosetron Hydrochloride | 0.005 |
| 3. | Dexamethasone Sodium phosphate | 0.24 |
| 4. | Kleptose | 100 |
| 5. | Meglumine | 1.904 |
| 6. | L-Aspartic acid | 2 |
| 7. | L-Arginine | 2 |

-continued

| S. No | Ingredients | mg/mL |
|---|---|---|
| 8. | Disodium EDTA | 0.05 |
| 9. | Sodium chloride | QS |
| 10. | Ultra-pure Water | QS to 1 mL |

QS: Quantity sufficient

Manufacturing Process:

Required quantity of L-Aspartic acid and L-Arginine were added to water followed by kleptose and stirred. Required quantity of meglumine, disodium EDTA and sodium chloride were added. The solution was cooled to 2-8° C. Fosaprepitant dimeglumine was added followed by Palonosetron hydrochloride and Dexamethasone sodium phosphate and stirred till a clear solution was obtained. The solution was filtered and filled in polyvinyl chloride bags.

Example 14

Ready to Use Formulation

| S. No | Ingredients | Quantity/mL (mg) |
|---|---|---|
| 1 | Fosaprepitant dimeglumine | 1.5 |
| 2 | Palonosertron hydrochloride | 0.0025 |
| 3 | Dexamethasone sodium phosphate | 0.08 |
| 4 | Kleptose (Hydroxy propyl betadex) | 100 |
| 5 | Meglumine | 1.904 |
| 6 | Aspartic acid | 2 |
| 7 | Arginine | 2 |
| 8 | Ethylenediaminetetraacetic acid | 0.05 |
| 9 | Sodium chloride | 3.5 |
| 10 | Water | Qs 1 mL |
|  | pH | 8.5 |

QS: Quantity sufficient

Manufacturing Process

Required quantity of Aspartic acid and L-Arginine were added to water followed by kleptose and stirred. Required quantity of meglumine, EDTA and sodium chloride were added. The solution was cooled to 2-8° C. Fosaprepitant dimeglumine was added followed by Palonosetron hydrochloride and Dexamethasone sodium phosphate and stirred till a clear solution was obtained. pH was adjusted to 8.5 and the solution was filtered and filled into 250 mL/500 mL infusion bags or bottles.

TABLE 7

Stability was carried out and the results are tabulated below

| Stability Condition | Initial | 1 month 2-8° c. | 12 Months 2-8° c. | 6 months 25° c. | 1 week 40° c. |
|---|---|---|---|---|---|
| pH | 8.58 | 8.55 | 7.59 | 8.53 | 8.67 |
| Description | Clear solution | Clear solution | Clear solution | Clear solution | Clear solution |
| Palonosetron | | | | | |
| % Assay | 103.0 | 102.0 | 105 | 103.4 | 102.0 |
| % Total Impurities | 0.14 | 0.43 | 0.15 | 0.87 | 0.38 |
| Dexamethasone | | | | | |
| % Assay | 100.4 | 99.4 | 102.4 | 98.5 | 100.2 |
| % Total Impurities | 0.69 | 1.04 | 2.0 | 1.7 | 1.04 |

TABLE 7-continued

Stability was carried out and the results are tabulated below

| Stability Condition | Initial | 1 month 2-8° c. | 12 Months 2-8° c. | 6 months 25° c. | 1 week 40° c. |
|---|---|---|---|---|---|
| Fosaprepitant | | | | | |
| % Assay | 102.2 | 101.1 | 103.8 | 104.4 | 100.9 |
| % Aprepitant | 0.31 | 0.48 | 0.63 | 4.72 | 1.84 |
| % Total Impurities | 0.39 | 0.75 | 0.66 | 4.87 | 1.91 |

Example 15

Ready to Dilute Formulation

| S. No | Ingredients | Quantity/ml (mg) |
|---|---|---|
| 1 | Fosaprepitant dimeglumine | 6 |
| 2 | Palonosertron hydrochloride | 0.01 |
| 3 | Dexamethasone sodium phosphate | 0.48 |
| 4 | Kleptose (Hydroxy propyl betadex) | 300 |
| 5 | Meglumine | 1.904 |
| 6 | Aspartic acid | 2 |
| 7 | Arginine | 2 |
| 8 | Ethylenediaminetetraacetic acid | 0.05 |
| 9 | Sodium chloride | 3.5 |
| 10 | Water | Qs 1 mL |
|  | pH | 8.5 |

Manufacturing Process

Required quantity of Aspartic acid and L-Arginine were added to water followed by kleptose and stirred. Required quantity of meglumine, EDTA and sodium chloride were added. The solution was cooled to 2-8° C. Fosaprepitant dimeglumine was added followed by Palonosetron hydrochloride and Dexamethasone sodium phosphate and stirred till a clear solution was obtained. pH was adjusted to 8.5 and the solution was filtered and filled into vials.

TABLE 8

Stability was carried out and the results are tabulated below

| Stability Condition | Initial | 1 month 2-8° c. | 6 Months 2-8° c. | 3 months 25° c. | 6 months 25° c. |
|---|---|---|---|---|---|
| pH | 8.5 | 8.53 | 7.83 | 8.51 | 7.95 |
| Description | Clear solution | Clear solution | Clear solution | Clear solution | Clear solution |
| Palonosetron | | | | | |
| % Assay | 100.3 | 99.8 | 103.7 | 100.2 | 103.1 |
| % Total Impurities | 0.15 | 0.39 | ND | 0.38 | 0.04 |
| Dexamethasone | | | | | |
| % Assay | 95.2 | 96.6 | 98.6 | 97.3 | 100.1 |
| % Total Impurities | 0.75 | 1.11 | 1.52 | 1.26 | 1.62 |
| Fosaprepitant | | | | | |
| % Assay | 97.3 | 98.1 | 96.0 | 96.3 | 93.4 |
| % Aprepitant | 0.41 | 0.54 | 0.75 | 2.78 | 4.6 |
| % Total Impurities | 0.55 | 0.63 | 0.80 | 2.96 | 4.67 |

The invention claimed is:
1. A parenteral formulation comprising:
    i. palonosetron;
    ii. a NK1 receptor antagonist selected from a group consisting of aprepitant, rolapitant, and fosaprepitant;

iii. a corticosteroid selected from dexamethasone and methylprednisolone; and
iv. pharmaceutically acceptable excipients.

2. The parenteral formulation of claim 1, wherein one or more of the pharmaceutically acceptable excipients are selected from a group consisting of stabilizing agents, solubilizing agents, buffering agents, pH adjusting agents, and solvents.

3. The parenteral formulation of claim 1, wherein total impurities are less than 10% w/w when stored at 2-8° C.

4. The parenteral formulation of claim 1, wherein
(a) the concentration of palonosetron ranges from 0.0005 mg/ml to 5 mg/ml,
(b) the concentration of the NK1 receptor antagonist ranges from 0.5 mg/ml to 100 mg/ml, and
(c) the concentration of dexamethasone ranges from 0.01 mg/ml to 50 mg/ml;
further wherein total impurities in the parental formulation are less than 10% w/w when stored at 2-8° C.

5. The parenteral formulation of claim 1, wherein
(a) the concentration of palonosetron ranges from 0.0005 mg/ml to 5 mg/ml,
(b) the concentration of the NK1 receptor antagonist ranges from 0.5 mg/ml to 100 mg/ml, and
(c) the concentration of methylprednisolone ranges from about 1 mg/ml to 100 mg/ml;
further wherein total impurities in the parenteral formulation are less than 10% w/w when stored at 2-8° C.

6. The parenteral formulation of claim 1, wherein the pH of the parenteral formulation ranges from 4 to 12.

7. The parenteral formulation of claim 1, wherein the pH of the parenteral formulation ranges from 6 to 10.

8. The parenteral formulation of claim 1, wherein the volume of the parenteral formulation ranges from 5 ml to 200 ml.

9. The parenteral formulation of claim 1, wherein the parenteral formulation is a ready to use solution.

10. The parenteral formulation of claim 1, wherein the parenteral formulation is a ready to dilute solution.

11. The parenteral formulation of claim 1, wherein the parenteral formulation is a lyophilized formulation.

12. The parenteral formulation of claim 2, wherein one or more buffering agents are selected from a group consisting of malic, succinic, aspartic acid, carbonic acid, alkali or alkaline earth salt of one of these acids, tris buffer, and amino acid buffers selected from the group consisting of arginine, histidine, glycine, lysine, and glutamic acid.

13. The parenteral formulation of claim 2, wherein one or more stabilizing or solubilizing agents are selected from a group consisting of surfactants, chelating agents, and cyclodextrins.

14. The parenteral formulation of claim 2, wherein the stabilizing or solubilizing agents are selected from a group consisting of cyclodextrins, ethylenediaminetetraacetic acid, meglumine, or mixtures thereof.

15. The parenteral formulation of claim 1, wherein the pharmaceutically acceptable excipients include one or more cyclodextrins and wherein the one or more cyclodextrins are selected from a group consisting of α, β, and γ-cyclodextrin and cyclodextrins modified with alkyl-, hydroxyalkyl-, dialkyl-, and sulfoalkyl-ether modified cyclodextrins such as methyl or hydroxypropyl β-cycl odextrins (HPOCD), methyl-and-ethyl β-cyclodextrin, sulfoalkyether-substituted beta-cyclodextrin, sulfobutylether-β-cyclodextrin (SBECD), and mixtures thereof.

16. The parenteral formulation of claim 2, wherein one or more pH adjusting agents are selected from a group consisting of acetic, boric, citric, lactic, phosphoric, and hydrochloric acids; sodium hydroxide, sodium phosphate, sodium borate, sodium citrate, sodium acetate, and sodium lactate.

17. The parenteral formulation of claim 2, wherein one or more solvents are selected from a group consisting of glycerine, ethanol, propylene glycol, PEG, dimethylacetamide, N-methylpyrrolidone, transcutol, glycofurol, water, and mixtures thereof.

18. A method of treating chemotherapy-induced nausea and vomiting comprising:
administering a pharmaceutically acceptable formulation, the pharmaceutically acceptable formulation comprising:
i. palonosetron,
ii. a NK1 receptor antagonist selected from a group consisting of aprepitant, rolapitant, and fosaprepitant,
iii. a corticosteroid selected from dexamethasone and methylprednisolone, and
iv. pharmaceutically acceptable excipients.

19. A parenteral formulation kit comprising:
i. palonosetron;
ii. a NK1 receptor antagonist selected from a group consisting of fosaprepitant, aprepitant, and rolapitant;
iii. a corticosteroid selected from dexamethasone and methylprednisolone; and
iv. pharmaceutically acceptable excipients;
wherein the palonosetron and the NK1 receptor antagonist are provided in the form of a solution and the corticosteroid is provided as a solution or lyophilized powder.

20. A parenteral formulation kit comprising:
i. palonosetron;
ii. a NK1 receptor antagonist selected from a group consisting of fosaprepitant, aprepitant, and rolapitant;
iii. a corticosteroid selected from dexamethasone and methylprednisolone; and
iv. pharmaceutically acceptable excipients;
wherein the palonosetron and the NK1 receptor antagonist are provided in the form of a solution and the corticosteroid is provided as a ready to use solution.

* * * * *